United States Patent [19]
Hyde et al.

[11] Patent Number: 5,318,527
[45] Date of Patent: Jun. 7, 1994

[54] FIXED WIRE CATHETER EXCHANGE DEVICE

[75] Inventors: Gregory M. Hyde, Sunnyvale; Jon A. Becker, Dublin; Kee S. Lee, Daly City, all of Calif.

[73] Assignee: Advanced Cardiovascular Systems, Inc., Santa Clara, Calif.

[21] Appl. No.: 995,478

[22] Filed: Dec. 22, 1992

[51] Int. Cl.⁵ ............................................. A61M 25/00
[52] U.S. Cl. ........................................ 604/95; 604/96; 128/772
[58] Field of Search .................. 604/96, 95, 280, 281, 604/282, 171, 164, 163; 606/194, 192; 128/656–658, 772

[56] References Cited

U.S. PATENT DOCUMENTS 5,131,407  7/1992  Ischinger et al. ............... 604/282 X
5,221,258  6/1993  Shturman ............................ 604/96

*Primary Examiner*—John D. Yasko
*Attorney, Agent, or Firm*—Crosby, Heafey, Roach & May

[57] ABSTRACT

A system for removing an in-place intravascular device such as a catheter or guidewire from a patient's body lumen such as from a coronary artery and advancing a catheter or other similar device through the vascular system until its distal end is located at a desired location within the vascular system. The system includes an exchange catheter, which may be a dilatation catheter, having a flexible strand forming a loop at the distal end of the catheter which is adapted to be disposed about the guidewire or catheter which is in-place within the patient. The loop is tightened about the elongated intraluminal in-place device to be removed so that the catheter can be advanced over the in-place device until the distal end of the catheter is at a desired location within the patient's vasculature. The catheter may be used to perform a diagnostic or therapeutic procedure such as an angioplasty or a replacement device may be advanced through an inner lumen and out the distal end of the catheter.

36 Claims, 1 Drawing Sheet

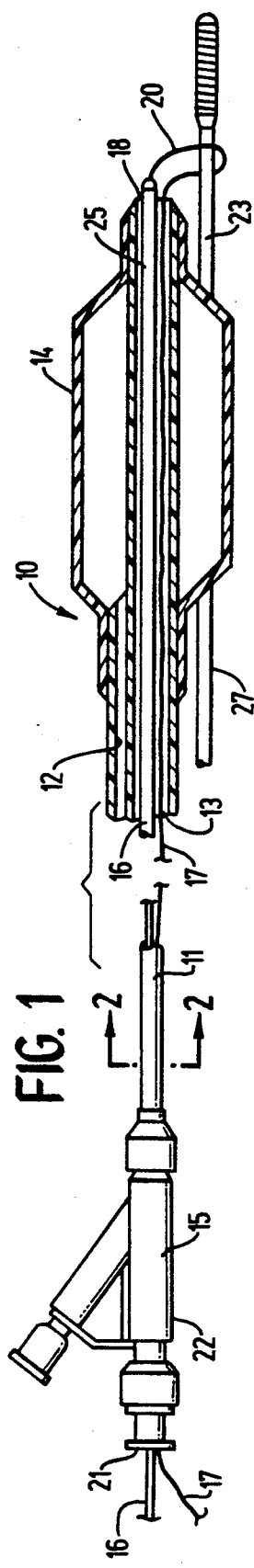
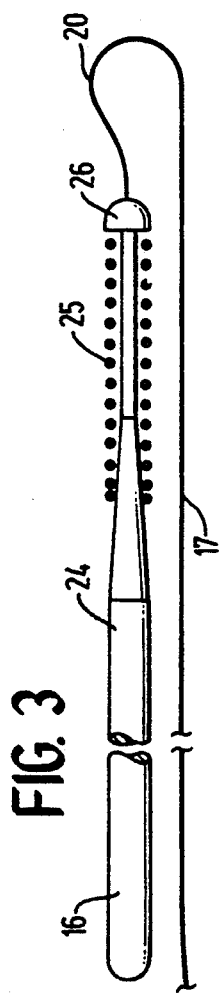
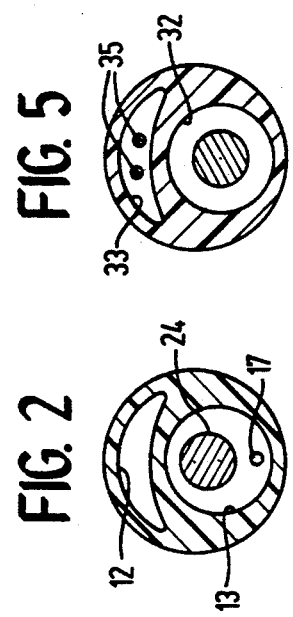
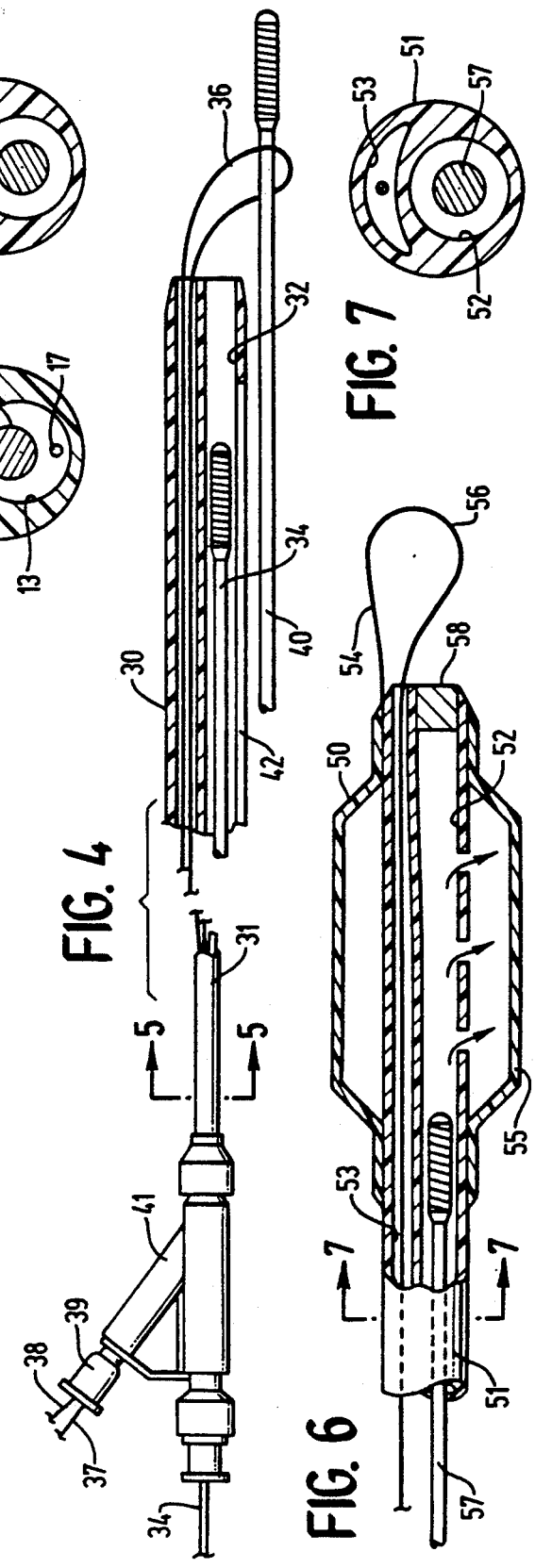

FIXED WIRE CATHETER EXCHANGE DEVICE

BACKGROUND OF THE INVENTION

This invention is generally related to intraluminal procedures such as coronary angioplasty procedures.

Percutaneous transluminal coronary angioplasty (PTCA) is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow therethrough. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced therein until the preshaped distal tip of the guiding catheter is disposed within the aorta adjacent the ostium of the desired coronary artery. The guiding catheter is twisted or torqued from the proximal end, which extends out of the patient, to guide the distal tip of the guiding catheter into the ostium. A balloon dilatation catheter may then be advanced through the guiding catheter into the patient's coronary artery until the balloon on the catheter is disposed within the stenotic region of the patient's artery. The balloon is inflated to open up the arterial passageway and increase the flow of blood.

One type of dilatation catheter frequently used in PTCA procedures is an over-the-wire type balloon dilatation catheter which has an inner lumen extending therein adapted to slidably receive a guidewire. When using an over-the-wire dilatation catheter, a guidewire is usually inserted into the inner lumen of the dilatation catheter before it is introduced into the patient's vascular system and then both the catheter and the guidewire are advanced through the guiding catheter to its distal tip which is seated within the ostium of the desired coronary artery. The guidewire is first advanced out the seated distal tip of the guiding catheter into the desired coronary artery until the distal end of the guidewire extends beyond the lesion to be dilatated. The dilatation catheter is then advanced out of the distal tip of the guiding catheter into the patient's coronary artery, over the previously advanced guidewire, until the balloon on the distal extremity of the dilatation catheter is properly positioned across the lesion to be dilatated. Once properly positioned across the stenosis, the dilatation balloon is inflated one or more times to a predetermined size with radiopaque liquid at relatively high pressures (e.g., generally 4–12 atmospheres) to dilate the stenosed region of a diseased artery. After the balloon inflations, it is finally deflated so that the dilatation catheter can be removed from the dilated stenosis and blood flow will resume. Commercial over-the-wire type dilatation catheters including the SIMPSON ULTRA LOW PROFILE ®, the HARTZLER ACX ®, the HARTZLER ACX II ®, the PINKERTON .018 TM and the ACS TEN TM balloon dilatation catheters are available from the assignee of the present invention, Advanced Cardiovascular Systems, Inc. (ACS).

Fixed-wire type dilatation catheter systems are also utilized very frequently in PTCA procedures. This type of dilatation catheter has a guidewire or guiding member secured within it. A fixed-wire dilatation catheter provides a low profile, i.e. small transverse dimensions, because it does not have an inner tubular member which is characteristic of commercially available over-the-wire dilatation catheters. Commercial fixed-wire dilatation catheters including the HARTZLER EXCEL ®, the HARTZLER LPS ® and the SLALOM TM dilatation catheters are available from ACS.

During an angioplasty procedure with an over-the-wire dilatation catheter, if there is a need to replace the dilatation catheter usually a guidewire extension wire such as disclosed in U.S. Pat. No. 4,827,941 is secured to the proximal end of the guidewire and the in-place dilatation catheter is withdrawn from the patient and removed from the guidewire and the extension wire. A replacement dilatation catheter is mounted onto the extension wire and advanced over the extension wire and the in-place guidewire to the desired location which is usually the prior location of the in-place catheter removed from the patient so that there is no loss of access to the desired location within the body lumen. While this catheter exchange procedure is widely practiced, it is not very convenient.

If a fixed-wire dilatation catheter within a patient needs to be exchanged for another catheter, e.g. because a different size balloon is needed, the only recourse with the prior art was to remove the in-place fixed-wire dilatation catheter from the patient and advance an over-the-wire/guidewire combination or another fixed-wire catheter. This option however, loses all access to the distal location of the original fixed-wire catheter. The guidewire or the fixed-wire catheter must be steered to the desired intraluminal location. In angioplasty procedures it is not uncommon to find that once the original catheter has been removed it is quite difficult, and sometimes impossible to advance a guidewire or fixed-wire catheter to the original location.

SUMMARY OF THE INVENTION

This invention is directed to an elongated intraluminal catheter and a method for using the intraluminal catheter which facilitates the withdrawal from a body lumen of an intraluminal device previously disposed therein without loss of access to the region of the body lumen about the distal end of the in-place intraluminal device.

The intraluminal catheter of the invention has an elongated shaft with proximal and distal ends and a flexible strand forming a loop extending from the distal end of the shaft. The loop, which need not be complete, i.e. at least a partial loop, is disposed about the in-place intraluminal device to be removed. The loop is preferably complete and is adjustable by means operable from the proximal of the shaft so that the loop can be tightened about the in-place intraluminal device disposed within a patient's body lumen to facilitate advancement of the catheter over the in-place device.

In a presently preferred embodiment the catheter has a shaft with at least one inner lumen extending within the catheter shaft from a discharge port in the distal end of the catheter shaft to a port at or near the proximal end of the catheter shaft. The flexible strand extends through the inner lumen and a portion of the strand extends out the distal port forming the loop exterior to the catheter.

To utilize the catheter, it is advanced over the in-place intraluminal device to a desired location within the patient's body lumen. Preferably, the loop is tightened about a proximal portion of the in-place device before the catheter is advanced within the patient. The in-place device is removed leaving the distal end of the catheter at a desired location within the patient's body lumen. The distal extremity of the catheter may be provided with means for performing diagnostic or therapeutic procedures, such as a dilatation balloon.

In one presently preferred embodiment the flexible strand is doubled throughout the inner lumen of the catheter with the free ends thereof extending out the proximal end of the catheter and a looped section extending out of a distal port in the distal end of the catheter. One of the free ends of the strand may be held and the other pulled proximally or both ends may be pulled proximally in order to tighten the looped section about an in-place intraluminal device. While the loop is tightened about the intraluminal device, it is not tightened to the extent that the catheter cannot be readily advanced over the in-place intraluminal device or the in-place device cannot be readily withdrawn.

In another presently preferred embodiment one of the free ends of the flexible strand is secured within the catheter with the other free end extending out of the proximal end of the catheter and a portion of the strand extending out of the distal port in the catheter to form the loop. The free end of the strand may be fixed, e.g. by a suitable adhesive, to the catheter, e.g. within the inner lumen or it may be fixed to an element held or secured within the inner lumen of the catheter.

The catheter may be in the form of a simple tubular element with a single lumen extending therethrough. In this case the tubular exchange device would act as tubular guide for a replacement device which is to be advanced into the body lumen. The catheter may also be a dilatation catheter, with the strand extending through the guidewire lumen of the dilatation catheter.

The present invention allows for the exchange of an elongated in-place intraluminal device, whether the device is a fixed-wire or an over-the-wire catheter or a guidewire, with another intraluminal device which can likewise be a fixed-wire or an over-the-wire catheter or a guidewire. Moreover, the exchanges can be effected with no loss of access to the region around the distal end of the in-place intraluminal device. These and other advantages of the invention will become more apparent from the following detailed description of the invention when taken in conjunction with the accompanying exemplary drawings.

BRIEF DESCRIPTION OF THE INVENTION

FIG. 1 is an elevational view, partially in section, of a dilatation catheter assembly embodying features of the invention.

FIG. 2 is a transverse cross-sectional view of the catheter assembly shown in FIG. 1, taken along the lines 2—2.

FIG. 3 is an enlarged elevational view, partially in section, of a guidewire-like member which is shown in FIG. 1 disposed within an inner lumen of the catheter and which has one end of the strand secured to the distal end thereof.

FIG. 4 is an elevational view, partially in section, of an alternate embodiment of the invention without an inflatable member on the distal extremity thereof.

FIG. 5 is a transverse cross-sectional view of the embodiment shown in FIG. 4 taken along the lines 5—5.

FIG. 6 is an elevational view, partially in section, of the distal portion of another alternate embodiment of the invention.

FIG. 7 is a transverse cross-sectional view of the embodiment shown in FIG. 6 taken along the lines 7—7.

DETAILED DESCRIPTION OF THE INVENTION

FIGS. 1 and 2 illustrate a dilatation catheter 10 embodying features of the invention which has an elongated catheter shaft 11, an inflation lumen 12, a guidewire receiving lumen 13, an inflatable member or balloon 14 and an adapter 15. Disposed within the guidewire receiving lumen 13 is a elongated guidewire-like stylet member 16 with a flexible strand 17 secured the distal end thereof which extends out of port 18 in the distal end thereof and forms a loop 20 exterior of the catheter 10. The free portion of the strand 17 extends through the guidewire receiving lumen 13 and out a port 21 in arm 22 of adapter 15. An in-place guidewire 23 is shown disposed within the loop 20 formed by the strand 17. An enlarged view of the guidewire-like stylet member 16, as shown in FIG. 3, has an elongated shaft 24 a flexible coil 25 disposed about the tapered distal extremity with a rounded plug 26 on the distal end thereof which secures one end of the strand 17 to the distal end of the guidewire-like stylet member 16.

To advance a catheter 10 over an in-place guidewire 23, the loop 20 of strand 17 is slipped over the proximal end of the guidewire which would extend out the proximal end of a guiding catheter extending out of the patient during an angioplasty procedure. The free end of the flexible strand 17 which extends out of the adapter port 21 in the adapter arm 22 is pulled proximally to tighten the loop about the core member 27 of the guidewire 23. The catheter 10 with the guidewire-like stylet member 16 disposed within the inner lumen 13 is advanced over the core member 27 of the in-place guidewire 23 until the distal end of the catheter 10 is positioned at a desired location within a patient's body lumen such as a coronary artery. Once the catheter 10 is in its desired position, the balloon 14 may be inflated to dilate the stenosis (not shown) within the patient's artery.

The in-place guidewire 23 may be withdrawn proximally, if it is to be replaced. It will be necessary to remove the stylet 16 from the guidewire lumen 13 before a replacement guidewire may be advanced therethrough and out the distal end of the catheter 10 into a desired location within the patient's body lumen. The catheter shaft 11 and the adapter 15 may be provided with in-line slits (not shown) to peel the catheter 10 off the replacement guidewire within the guidewire lumen 13.

An alternative embodiment of the invention is depicted in FIGS. 4 and 5 which is similar to the embodiment shown in FIG. 1 but without an inflatable member and a guidewire-like stylet member. In this embodiment the catheter 30 has a shaft 31 with inner lumens 32 and 33. Lumen 32 is adapted to slidably receive a replacement member such as guidewire 34 and lumen 33 is adapted to receive the doubled flexible strand 35 which forms a loop 36 exterior to the distal end of the shaft 31 and which free ends 37 and 38 extending out the adapter arm 39. An in-place guidewire 40 is shown extending through the loop 36.

The operation of this embodiment is essentially the same as the embodiment shown in FIGS. 1-3. The loop 36 is tightened about the in-place guidewire 40 and the exchange catheter 30 is advanced over the in-place guidewire to the desired location within a patient's vasculature. The catheter 30 is not necessarily designed to perform diagnostic or therapeutic procedures, although modifications can be made to the catheter for such purposes. In a presently preferred embodiment the shaft 31 and adapter 41 are provided with a slits 42 and 43 respectively to facilitate peeling the catheter 30 off the replacement guidewire.

FIGS. 6 and 7 illustrate yet another alternative embodiment of the invention which has an exchange catheter 50 very similar to that shown in FIG. 1. In this embodiment the catheter 50 has an elongated shaft 51, a first guidewire receiving and inflation lumen 52 and a second lumen 53 which is adapted to receive flexible strand 54. One end of the strand 54 is secured between the junction of the distal end of the balloon 55 and the distal end of the shaft 51 which extends through the interior of the balloon. The strand 54 forms the loop 56 outside the distal end of the shaft 51 with the rest of the strand 54 extending through the second lumen 53 and out an arm of an adapter (not shown) on the proximal end of the shaft 51, such as shown in FIG. 1. The portion of the strand 54 extending out of the adapter arm is pulled to tighten the loop 56 to facilitate the advancement of the exchange catheter over an in-place guidewire or other elongated member to the desired location within the patient's artery in the manner previously described. A guidewire or mandrel 57 is disposed within the lumen 52 and acts as a stylet to urge the catheter through a patient's vasculature. A plug 58 blocks off the distal end of the lumen 52.

The various components of the exchange system of the invention can be made from conventional components. For example the catheter shaft and balloon can be formed of polyethylene, polyvinyl chloride, polyethylene terephthalate, polyolephin ionomers, e.g. Surlyn ®. The guidewire like member illustrated with the embodiment of FIGS. 1-3 may be formed at least in part of stainless steel or a superelastic NiTi alloy. The strand which forms the loop may be formed of a variety of flexible high strength materials such as a superelastic NiTi alloy, nylon, aramid. Preferably, the strand is formed from an alloy consisting essentially of about 30 to about 52% titanium and the balance nickel and up to 10% of one or more additional alloying elements. Such additional alloying elements may be selected from the group consisting of up each in amounts up to 10% iron, cobalt, chromium, platinum and palladium in amounts up to 3% each and copper and vanadium in amount of up to 10% each. As used herein all references to percent composition are atomic percent unless otherwise noted. To form the elongated superelastic strand an elongated solid rod or wire of the preferred alloy material is first cold worked, preferably by drawing, to effect a size reduction of about 30% to about 70% in the transverse cross section thereof. The cold worked material may then be given a heat treatment at a temperature of about 350° to about 600° C. for about 0.5 to about 60 minutes. If a material with a straight memory is desired the cold worked wire is subjected to a longitudinal stress equal to about 5% to about 50%, preferably about 10% to about 30%, of the yield stress of the material (as measured at room temperature) during the heat treatment. The cold worked and heat treated alloy material has an austenite finish transformation temperature of about −20° to about 40° C., i.e. less than body temperature and preferably about −10° to about 30° C. For more consistent final properties, it is preferred to fully anneal the solid rod or wire prior to cold work so that the material will always have the same metallurgical structure at the start of the cold working and so that it will have adequate ductility for subsequent cold working. It will be appreciated by those skilled in the art that means of cold working the metal other than drawing, such as rolling or swaging, can be employed. The ultimate tensile strength of the superelastic material is well above 200 ksi with an ultimate elongation at failure of about 15%. The material exhibits a stress-induced austenite-to-martensite phase transformation over a broad region of strain at a very high, relatively constant stress levels. As a result a strand formed of this material is very strong and very flexible.

While the present invention has been described herein in terms of an elongated device for exchanging guidewires, the invention can be utilized to exchange a variety of intravascular devices such as over-the-wire and fixed-wire catheters and including rapid exchange type catheters. Additionally, the invention can be employed with a variety intravascular exchange devices, including atherectomy, laser angioplasty, imaging and diagnostic devices. Those skilled in the art will recognize that various modifications and improvements can be made to the invention without departing from the scope thereof.

What is claimed is:

1. An intraluminal system for removing an elongated device, which has proximal and distal ends and which is disposed within a patient's body lumen, without loss of access to a lumenal region about the distal end of the elongated device, comprising:
    a) an elongated exchange member having proximal and distal ends; and
    b) a flexible strand extending from the distal end of the exchange member and forming at least a partial loop which is configured to be disposed about and slidable over the elongated device to be removed to facilitate advancement of the exchange member over the elongated device to a desired location within the patient's body lumen.

2. The intraluminal system of claim 1 wherein the strand forms essentially a complete loop.

3. The intraluminal system of claim 1 including means to tighten the loop about the elongated device to be removed.

4. The intraluminal system of claim 3 wherein the means to tighten the loop adjusts the length of the loop.

5. The intraluminal system of claim 3 wherein the means to tighten the loop is operable from the proximal end of the exchange member.

6. The intraluminal system of claim 1 wherein the flexible strand is formed of a superelastic alloy.

7. The intraluminal system of claim 6 wherein the superelastic alloy consists essentially of about 30 to about 52% titanium and the balance nickel and up to about 10% of one or more additional alloying elements selected from the group consisting of iron, cobalt, chromium, platinum and palladium in amounts of up to about 3% each and copper and vanadium in amounts up to about 10 each.

8. The intraluminal system of claim 1 wherein the elongated exchange member has an inner lumen extending proximally from a port in the distal end of the exchange member.

9. The intraluminal system of claim 8 wherein at least one length of the flexible strand extends within the inner lumen.

10. The intraluminal system of claim 8 wherein an elongated stylet is slidably disposed within the inner lumen of the exchange member and an end of the flexible strand is secured to a distal portion of the stylet.

11. The intraluminal system of claim 8 wherein at least one length of the strand extends through the inner lumen to the proximal end of the elongated exchange member.

12. The intraluminal system of claim 11 wherein the flexible strand has an end secured to a distal portion of the exchange member.

13. An intraluminal system for advancing an elongated catheter over on elongated intraluminal device disposed within a patient's body lumen to a lumenal region about a distal portion of the elongated intraluminal device comprising:
   a) an elongated catheter having proximal and distal ends and an inner lumen extending therein to a port in the distal end thereof;
   b) an elongated flexible strand disposed within the inner lumen of the catheter with a portion of the strand extending out the port in the distal end of the catheter and forming a loop exterior thereto adapted to be disposed about the elongated intraluminal device disposed within the patient's body lumen to facilitate advancement of the catheter over the elongated intravascular device to a desired location within the patient's body lumen.

14. The intraluminal system of claim 13 including an elongated stylet extending within the inner lumen of the elongated catheter.

15. The intraluminal system of claim 14 wherein an end of the flexible strand is secured to a distal portion of the stylet.

16. The intraluminal system of claim 13 wherein a portion of the strand extends through the inner lumen of the catheter.

17. The intraluminal system of claim 16 wherein the portion of the flexible strand extending through the inner lumen of the catheter has a free end extending out the proximal end of the catheter which may be pulled to tighten the loop about the elongated intraluminal member.

18. The intraluminal system of claim 13 wherein the catheter has means on a distal portion to perform an intraluminal procedure.

19. The intraluminal system of claim 18 wherein the means for performing an intraluminal procedure is a dilatation balloon which has an interior in fluid communication with an inflation lumen extending through the catheter.

20. A method of advancing a catheter over an elongated intravascular device disposed within a patient's vascular system comprising:
   a) providing an elongated catheter having proximal and distal ends, a first inner lumen extending therein to a first port in the distal end of the catheter, a flexible strand extending from the distal end of the catheter and forming a loop exterior thereto;
   b) disposing the loop formed by the flexible strand about the intravascular device disposed within the patient's vascular system; and
   c) advancing the catheter within the patient's vascular system with the loop formed by the flexible strand sliding over the intravascular device disposed within the patient's vascular system until the distal end of the catheter is at a desired location within the patient's vascular system.

21. The method of claim 20 including withdrawing the elongated intravascular device from the patient's vascular system leaving the catheter in place.

22. The method of claim 20 wherein the loop is tightened about the intravascular device before the catheter is advanced over the intravascular device.

23. The method of claim 21 including advancing a replacement intravascular device through a second inner lumen of the catheter until the replacement device extends out of the distal end of the catheter.

24. A method for performing an angioplasty procedure within a patient's artery, comprising:
   a) providing an elongated dilatation catheter having proximal and distal ends, a first inner lumen extending therein to a first port in the distal end of the dilatation catheter, an inflatable dilatation balloon on a distal portion of the dilatation catheter, a second inner lumen extending therein to an interior of the balloon, and a flexible strand which extends through the first inner lumen and out of the port in the distal end of the dilatation catheter and which forms a loop exterior thereto;
   b) disposing a proximal portion an intravascular device disposed within the patient's artery within the loop;
   c) advancing the dilatation catheter into and within the patient's artery, with loop sliding on the intravascular device, until the distal end of the dilatation catheter is located at a desired location within the patient's artery; and
   d) inflating the dilatation balloon within a stenosis within the patient's artery to perform an angioplasty procedure.

25. The method of claim 24 including withdrawing the elongated intravascular device from the patient's artery, leaving the dilatation catheter in place.

26. The method of claim 24 wherein the loop is tightened about the elongated intravascular device before advancing the dilatation catheter within the patient's artery.

27. The method of claim 25 wherein a replacement intravascular device is advanced through the first inner lumen, out the port in the distal end of the dilatation catheter into the patient's artery.

28. The method of claim 27 wherein the replacement intravascular device is a guidewire.

29. The method of claim 28 wherein the dilatation catheter is advanced further within the patient's artery over the replacement guidewire.

30. A balloon dilatation catheter assembly, comprising:
   a) an elongated catheter shaft having proximal and distal ends, a first inner lumen extending therein to a port in the distal end of the shaft and a second inner lumen extending therein to a location proximal to the distal end of the shaft;
   b) an expandable dilatation balloon on a distal portion of the catheter shaft having an interior in fluid communication with the second inner lumen;
   c) a flexible strand disposed within the first inner lumen with a portion of the strand extending out the port in the distal end of the catheter shaft and forming a loop which is adapted to be mounted about an elongated intravascular device disposed within the patient's artery to facilitate advancement of the catheter over the elongated intravascular device to a desired location within the patient's artery.

31. The balloon dilatation catheter of claim 30 wherein an elongated stylet is disposed within the first inner lumen and an end of the flexible strand is secured to a distal portion of the stylet.

32. A stylet suitable for disposition within an inner lumen of an intravascular catheter, comprising:
   a) an elongated core member having a tapered distal portion;
   b) a flexible member having proximal and distal ends and being secured to the tapered distal portion of the core member;
   c) an elongated flexible strand having one end secured to the distal end of the flexible member.

33. The stylet of claim 32 wherein the flexible strand is formed of a superelastic alloy.

34. The stylet of claim 33 wherein the superelastic alloy contains titanium and nickel.

35. The stylet of claim 33 wherein the superelastic alloy consists essentially about 30 to about 52% titanium and the balance nickel and up to 10% other alloying elements.

36. The stylet of claim 35 wherein the other alloying element are selected from the group consisting of iron, cobalt, chromium, platinum and palladium in amounts of up to 3% each and copper and vanadium in amount of up to 10% each.

* * * * *